(12) United States Patent
Posseme et al.

(10) Patent No.: US 7,932,078 B2
(45) Date of Patent: Apr. 26, 2011

(54) DIRECT INOCULATION METHOD USING FROZEN CONCENTRATED CULTURES AND ASSOCIATED DEVICE

(75) Inventors: Jean-Paul Posseme, Villejuif (FR); Jean-Claude Bercetche, Saint Jean Pied de Port (FR); Jean-Marie Odinot, Remereville (FR)

(73) Assignee: CHR-Hansen A/S, Horsholm (DK)

( * ) Notice: Subject to any disclaimer, the term of this patent is extended or adjusted under 35 U.S.C. 154(b) by 1123 days.

(21) Appl. No.: 11/632,484

(22) PCT Filed: Jul. 8, 2005

(86) PCT No.: PCT/EP2005/053278
§ 371 (c)(1),
(2), (4) Date: Jan. 16, 2007

(87) PCT Pub. No.: WO2006/008245
PCT Pub. Date: Jan. 26, 2006

(65) Prior Publication Data
US 2008/0145481 A1   Jun. 19, 2008

(30) Foreign Application Priority Data
Jul. 21, 2004   (FR) ..................................... 04 08080

(51) Int. Cl.
*C12M 1/36*   (2006.01)
*C12M 1/38*   (2006.01)
*C12M 3/00*   (2006.01)

(52) U.S. Cl. ........... 435/286.5; 426/34; 426/42; 426/43; 435/252.1; 435/252.9; 435/289.1

(58) Field of Classification Search .................... 426/34, 426/36–43, 582; 435/252.1–252.9, 286.5, 435/289.1–297.2
See application file for complete search history.

(56) References Cited

U.S. PATENT DOCUMENTS

| | | | | |
|---|---|---|---|---|
| 5,979,300 | A | * | 11/1999 | Donovan ......................... 99/323 |
| 2001/0024667 | A1 | * | 9/2001 | Smith et al. ..................... 426/36 |
| 2001/0049132 | A1 | * | 12/2001 | Kringelum et al. ......... 435/252.4 |
| 2002/0054936 | A1 | * | 5/2002 | Hoier et al. ...................... 426/61 |
| 2003/0031755 | A1 | * | 2/2003 | Hoier et al. ...................... 426/43 |

FOREIGN PATENT DOCUMENTS

| | | |
|---|---|---|
| EP | 0 688 864 A1 | 12/1995 |
| WO | WO 99/09838 | 3/1999 |
| WO | WO 01/70935 | 3/2001 |
| WO | WO 02/024870 A1 | 9/2001 |
| WO | WO 03/011039 A1 | 2/2003 |

\* cited by examiner

*Primary Examiner* — Walter D Griffin
*Assistant Examiner* — Shanta G Doe
(74) *Attorney, Agent, or Firm* — Stephen A. Bent; Foley & Lardner LLP (57) ABSTRACT

A device for the continuous dosage of frozen starter cultures into a liquid fermentation medium is provided. The device comprises a fermentation unit and a container for the thawing of the starter cultures. It further comprises means of retaining the frozen cultures inside the thawing container while allowing the culture in liquid form to feed into a circuit for continuously feeding the fermentation medium to be inoculated. Furthermore, a method of dosing a frozen inoculant into a liquid fermentation medium is also described.

20 Claims, 8 Drawing Sheets

DIRECT INOCULATION METHOD USING FROZEN CONCENTRATED CULTURES AND ASSOCIATED DEVICE

The objective of the present invention is to provide a continuous inoculation device using frozen concentrated cultures and which do not require neither incubation, preculturing nor activation, which is potentially risky from a microbial purity point of view, and which may interrupt the inoculation process during manufacture. Another object of the invention is an inoculation method using the method according to the invention.

The preparation of most dairy products involves the use of microorganisms, in particular the group of bacteria generally referred to as lactic acid bacteria. As used herein the term "lactic acid bacterium" designates a gram-positive, microaerophilic or anaerobic bacterium, which ferments sugars with the production of acids including lactic acid as the pre-dominantly produced acid, acetic acid and propionic acid. The industrially most useful lactic acid bacteria are found among *Lactococcus* spp., *Streptococcus* spp., *Lactobacillus* spp., *Leuconostoc* spp., *Pediococcus* spp., *Brevibacterium* spp. and *Propionibacteium* spp. Additionally, lactic acid producing bacteria belonging to the group of the strict anaerobic bacteria, bifidobacteria, i.e. *Bifidobacterium* spp., which are frequently used as food cultures alone or in combination with lactic acid bacteria, are generally included in the group of lactic acid bacteria. Lactic acid bacteria are essential in the making of nearly all fermented milk products, cheese and butter, and they are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product. Such cultures are in general referred to as "starter cultures" or "starters".

In the fermentation process the process of inoculation is of prime importance because the industrial and qualitative performance of the end products depends on the nature and efficacy of the starter cultures used and their method of addition.

The use of the starter culture obtained from a mother culture of bacteria (mother liquor) requires the provision, maintenance and functioning of dedicated equipment. In addition, compliance with strict instructions, in particular with regard to hygiene, and full control of the fermentation parameters for the starter is essential.

Due to their high activity and their advantageous technological performance, frozen starter cultures are gaining a wider use in the dairy industry. However, certain disadvantages are associated with the use of pellets of frozen or freeze-dried DVS cultures, particularly with small vat sizes. For instance pellets of frozen or freeze-dried DVS cultures require a high degree of manual handling since the DVS culture has to be weighed out manually and then added separately to each vat. Furthermore, because of a need for rapid filling and inoculation, particularly in soft cheese production, the manual addition of solid DVS cultures often represents a significant organizational and coordinational challenge regarding the planning of the working schedule for the staff, which eventually results in higher production costs; and finally, a high degree of manual handling increases the risk of contamination considerably.

Methods using prior activation of the culture in order to reduce the lag phase and thus allow more rapid initiation of the bacterial growth during inoculation have been described. The provision of starter cultures for inoculation of milk is known from the documents WO 200170935 and EP688864. WO99/09838 describes a method for preparing a fresh dairy product comprising the steps of supplying a starter culture, which may be in frozen form, and mixing this culture with an aqueous medium in order to obtain a microbial culture suspension serving to inoculate milk in a container. WO99/09838 also describes containers for these starter cultures for inoculation of the aqueous medium in situ under acceptable aseptic conditions.

WO03/011039 describes an apparatus used for preparing a dairy product in which the starter culture is previously mixed with the milk and preincubated before being used for inoculating the fermentation media in the fermentation vessel for manufacturing a dairy product.

Finally, WO 02/24870 describes an inoculation method, which results in "a significant reduction of the latency period" of the starter cultures before inoculation. The application describes a starter culture based on lactic bacteria that is in contact with an activator for a certain time prior to its introduction into the milk medium to be used. A method of preparing a milk product characterized by the inoculation of an activated culture continuously into a culture is also described.

These reactivation and/or dilution systems have the disadvantage of requiring a high degree of manual handling of the concentrated starter cultures before the actual inoculation is performed. For example, these systems are dependent on weighing or preculturing of the starter steps, which increases the risks of contamination.

Moreover, the fermentation of the liquid medium to be inoculated by frozen concentrated cultures forces the industrial user to work discontinuously during the inoculation and fermentation phases. Due to the form and type of the packaging, which generally is bags or boxes, the addition of the microorganisms must necessarily be carried out directly into the fermentation vessel.

It appears from the above that there is a clear need in the market for a method and an apparatus that diminish the inter batch quality variation of the products, shorten the production time for fermented dairy products, facilitate the planning and management of the production work and reduce the production costs.

The inventors of the present invention have surprisingly found a novel method and a novel apparatus that meet these requirements. The present invention will be described below by disclosing a method and an apparatus in more detail.

According to a first aspect of the invention, a device for the continuous dosage of frozen starter cultures into a liquid fermentation medium is provided. The device comprises a fermentation unit and a container for the thawing of the starter cultures. It further comprises means of retaining the frozen cultures inside the thawing container while allowing the culture in liquid form to proceed through an outlet opening (outlet orifice) to feed into a circuit for continuously feeding of the fermentation medium to be inoculated into a fermentor (fermentation unit). The conduit (or pipe) feeding the liquid starter culture to the conduit feeding the fermentation medium into the fermentor is provided with means of regulating the flow rate of the cultures in liquid form and the flow-rate of the fermentation medium.

A device for the continuous dosage of frozen starter cultures into a liquid fermentation medium is provided. The device comprises a fermentation unit and a container for the thawing of the starter cultures. It further comprises means of retaining the frozen cultures inside the thawing container while allowing the culture in liquid form to feed into a circuit for continuously feeding the fermentation medium to be inoculated. Furthermore, a method of dosing a frozen inoculant into a liquid fermentation medium is also described.

By the term "fermentation unit" is referred to a fermenter, i.e. a vessel or container suitable for performing the actual fermentation of the fermentation medium (fermentation substrate) to be converted by the organisms of the starter culture, e.g. milk. Both large-scale fermentation vessels as well as small-scale containers used to perform the actual fermentation of the substrate and intended to be sold are referred to as a "fermentation unit". In the case of a dairy product the fermentation unit may, for example, be a dairy product cup.

The applicants have surprisingly discovered that the introduction of frozen concentrated cultures can be carried out in a direct and continuous inoculation process. This process avoids both the problematic starter culture preparation step and also allows continuous inoculation without being forced to interrupt the fermentation process for manufacturing the end product. It thus becomes possible to substantially increase production rates of the fermented product. In addition, this continuous inoculation method further ensures a uniform quality of the end products. Furthermore, the invention allows the frozen concentrated cultures to be used directly from the container by pouring directly into the thawing and/or storage container without an intermediate step, which would increase the risk of contamination. Any additional manual handling operation inevitably increases the risks of accidental contamination, which is damaging to the entire subsequent process of manufacturing the fermented product.

These frozen concentrated cultures can be packed and preserved in packages of greater or lesser capacity varying from 200 g to several kg. The transfer must take place under strict hygienic or aseptic conditions in order to prevent any contamination, which is damaging to the entire subsequent fermentation process.

In preferred embodiments the frozen starter culture is provided in a flexible enclosure that is designed to fit inside the thawing container. The flexible enclosure may conveniently be designed as a sealable bag having an opening for loading with starter culture and means permitting the enclosure to be mounted within the thawing container onto the conduit of the dosage device. After loading the flexible enclosure with the starter culture the enclosure is sealed and used to distribute the frozen starter culture to the end user. The flexible enclosure can be evacuated prior to being sealed air tightly whereby the enclosing packaging will fill up as little as possible. Evidently, this facilitates distribution and reduces the requirement for storage space significantly. The enclosure may also be filled with a sterile inert gas prior to sealing. Furthermore, the sealed enclosure can be provided with means, e.g. a rigid mesh or grille equipped with openings, ensuring that when mounted onto the dosage device the frozen concentrated cultures are retained inside the sealed enclosure whereas the melted culture are fed into the device. In one embodiment the sealed enclosure are provided with a threaded outlet means to permit screw connection of the enclosure to the device, thus providing a substantially aseptical introduction of the starter culture suspension into the fermentation unit. The screw connection can be further protected against any damage under transportation with a screw cap, which is removed prior to the connection of the enclosure to the device. In a specific embodiment, the outlet means of the enclosure comprise one or more layers of a metal foil, such as an aluminium foil, to prevent introduction of atmospheric air into the sealed enclosure.

This flexible enclosure preferably consists of a flexible material such as, for example, polypropylene, polyester, polyamide, cellulose or any other flexible material compatible with starter cultures, preferably it is made of polyethylene. The flexible material may comprise one or more layers of a polymeric material, which is compatible with the use in a food production method, and such polymers can be selected from a polyolefin, a substituted olefin, a copolymer of ethylene, a polyester, a polycarbonate, a polyamide, an acrylonitrile and a cellulose derivative, or a mixture thereof. In useful embodiments the material may be made of at least two layers of polymers such as at least three layers. Additionally, the flexible enclosure material may comprise a metal foil or at least one layer of paper, optionally in combination with one or more layers of polymer in the form of composite materials.

The enclosure which functions as packaging for the starter culture, can be of any design, configuration or shape and can be made of any material which is compatible with the usage as containment of starter cultures, i.e. the material must be non-toxic to the culture organisms and it must be of a food grade type and quality.

The use of such a flexible container for the distribution of frozen starter cultures will reduce the risk of contamination even further.

The frozen concentrated cultures used are composed of bacteria, typically lactic acid bacteria, used for the manufacture of cheeses such as for example soft cheeses, hard and semi-hard cheeses, uncooked pressed cheeses, stretched-curd cheeses and fermented milks such as for example flavoured or natural yoghurts, (both stirred or set), drinking yoghurts, crème fraîche, sour cream, quark and fromage frais, and for the manufacture of other fermented products such as for example wine.

The invention can be used with any type of microorganism that can be provided as frozen concentrated starter cultures. Lactic acid bacteria as well as other types of bacteria are frequently provided as frozen concentrated cultures. However, it is contemplated that most cultures of microorganisms, including cultures of yeast and certain fungi may be provided as frozen concentrated cultures and thus used with the present invention.

Specifically the frozen concentrated culture may be a culture of mesophilic microorganisms whose optimal temperature is between 25° and 35° C. Examples of the mesophilic microorganisms typically used are *Lactococcus lactis* subsp. *lactis, Lactococcus lactis* subsp. *cremoris, Leuconostoc cremoris, Lactococcus lactis* biovar. *diacetylactis, Lactobacillus casei, Streptococcus durans* and *Streptococcus faecalis*.

The present invention may also be used with cultures of thermophilic microorganisms, i.e. organisms with an optimal temperature between 35° and 45° C. Examples of useful thermophilic microorganisms are *Streptococcus thermophilus, Lactobacillus lactis, Lactobacillus helveticus; Lactobacillus delbrueckii* subsp. *bulgaricus* and *Lactobacillus acidophilus* or any other suitable microorganism.

The invention is particularly useful with cultures of strictly anaerobic microorganisms of the bifidobacteria genus including *Bifidus bifidum* and *Bifidobacterium longum* (animalis) since it is possible to keep the whole system under low oxygen tension. It is contemplated that the use of the present invention with a culture of strictly anaerobic microorganisms packed in a flexible bag filled with a sterile inert gas is particularly advantageous.

It is also possible to use the invention with cultures of propionic bacteria such as *Propionibacterium freudenreichii* or *Propionibacterium freudenreichii* subsp. *shermanii*.

In a further embodiment of the invention, the invention is used with cultures of wine fermenting bacteria, for example *Oenococcus oeni* (*Leuconostoc oenos*), *Lactobacillus plantarium* or *Pediococcus* sp.

In one particular embodiment, the inoculation device or method of the invention is used in the process of producing starter cultures.

Furthermore, it is contemplated that the invention is useful for the production of other types of fermentations depending on the particular type of frozen starter cultures and the medium sought to be fermented.

In one preferred embodiment the inoculated liquid fermentation medium is kept under starter culture fermenting conditions to obtain a fermented beverage, food or feed product. The method is particularly useful to obtain a fermentation of milk, milk derived products, wine, juice or even silage. It is contemplated that the present invention is particularly useful when the frozen concentrated cultures are selected from the group of cultures consisting of frozen cultures of lactic acid bacteria, however the invention can be used with other bacteria cultures and even with frozen cultures of yeasts and other microorganisms.

In one preferred embodiment, the device comprises an intermediate storage container or device for the cultures interposed between the thawing container and the means of regulating the flow rate of the liquid starter culture.

As illustrated by the example this storage container or device makes it possible to keep the thawed cultures in a form, which is suitable for inoculating the fermentation media directly in the fermentation unit.

The thawing container can be connected to the storage container by a removable connection.

This type of connection thus provides easy removal of the thawing container from the rest of the device in order to allow easy cleaning and/or sterilization of the thawing container.

The continuous inoculation device may comprise means of mixing the cultures with some of the fermentation medium to be inoculated. It is advantageous to mount said means of mixing in the circuit downstream of a flow rate regulation means.

The thawing container of this device can advantageously comprise heating means.

The intermediate storage container can comprise refrigeration means.

The storage container can for example comprise a double wall (water jacket) allowing the circulation of a cooling liquid, which for example may be ice water. The storage of the thawed liquid cultures thus takes place at a relatively low temperature, which may be between 2 and 12° C., or any other temperature compatible with maintaining the activity of the culture.

This storage container may have a stirrer in the container for intermediate storage of the thawed cultures. The appearance and characteristics of the melted cultures are variable according to the microorganism species or mixtures of species in question, the texture and more particularly the viscosity of the melted starter cultures are of particular importance for the correct performance of the dosage. In addition, the storage temperature within the storage container must typically be maintained between 2 and 12° C., preferably between 2 and 5° C. in order to limit the resumption of the metabolism of the microorganism sufficiently to ensure that the quality of the inoculant is constant over time. Further, to ensure a constant quality of the inoculant over time the storage container may be provided with means of stirring of the melted mixture thus ensuring homogeneity of the liquid starter culture.

In one embodiment of the invention, the device comprises a circuit for feeding the liquid to be inoculated. The device is connected as a bypass of the main circuit, which feeds the fermentation unit. Since a continuous industrial process by definition should not be interrupted by manual operations this bypass of the main feed line for the fermentation medium to be inoculated is necessary.

The level of inoculation with concentrated bacterial cultures or frozen concentrated cultures varies according to the technologies and products in question. In general terms, this proportion is between 0.005 and 0.025% of the total mass of the medium to be inoculated.

In the situation where the volume of fermentation unit is small such as in the situation where the fermentation unit is a container intended to be sold to the end-user, a dairy product cup, for example, an optional, extra storage container may be inserted between the outlet of the main feed line for the fermentation medium and the fermentation unit to obtain a homogeneous product.

The invention also concerns a method of dosage of a liquid inoculation in which the frozen concentrated cultures are thawed, kept temporarily at a low temperature and then a dosed quantity of thawed concentrated cultures is introduced continuously into a flow of liquid to be inoculated.

The time period of which these frozen concentrated cultures are kept in the thawing container is variable according to the quality and quantity of product added to the container. Typically, the thawing time of a frozen starter culture is between 10 and 60 minutes at a temperature (of the water jacket) in the double wall of the thawing container not exceeding 45° C. in order to avoid stressing the bacteria present in the concentrated cultures. The temperature of the ambient atmosphere in the thawing container should be between 20° and 30° C. and preferably 25° C. in order to ensure rapid melting of the concentrated cultures without creating any significant thermal shock, which may be damaging to the correct performance of the subsequent phases of the manufacturing method.

In one embodiment of the invention, the thawing container is put under positive pressure (i.e. a pressure that is higher than the pressure of the environment surrounding the device). The positive pressure may conveniently be obtained by injecting an inert sterile gas into the device. Such a positive pressure will facilitate the flow of the melted concentrated culture to the storage container and help to maintain the pressure therein as constant as possible. This will facilitate the precision of the dosage of the concentrated starter cultures. In addition, a positive pressure in the thawing container limits the possibilities of contamination by external air. An overpressure of typically 100 g/cm$^2$ allows a more constant dosage.

The invention is further illustrated in the following examples and the drawings wherein:

In FIG. 1 (1) designates a thawing container, (1a) the frozen concentrated culture, (3) the conduit of the frozen concentrated culture, (5) of the conduit feeding the fermentation medium to be inoculated, (6) a means for retaining the frozen concentrated cultures inside the thawing container while allowing the thawed culture to pass into an inoculation conduit (3), (10) a connector connecting (1) to (3), (13) the fermentation unit, (14) an optional flow meter, (17) and (19) dosage pumps, (20) an optional mixing chamber and (21) inlet for the cultures.

In order to fully understand the principles and aspects of the present invention, a detailed description of a preferred embodiment hereof will be given in the following. An example of such preferred embodiment of the invention is shown in FIG. 2, which is a schematic representation of apparatus for inoculating a fermentation unit in accordance with the invention.

Figure 1:
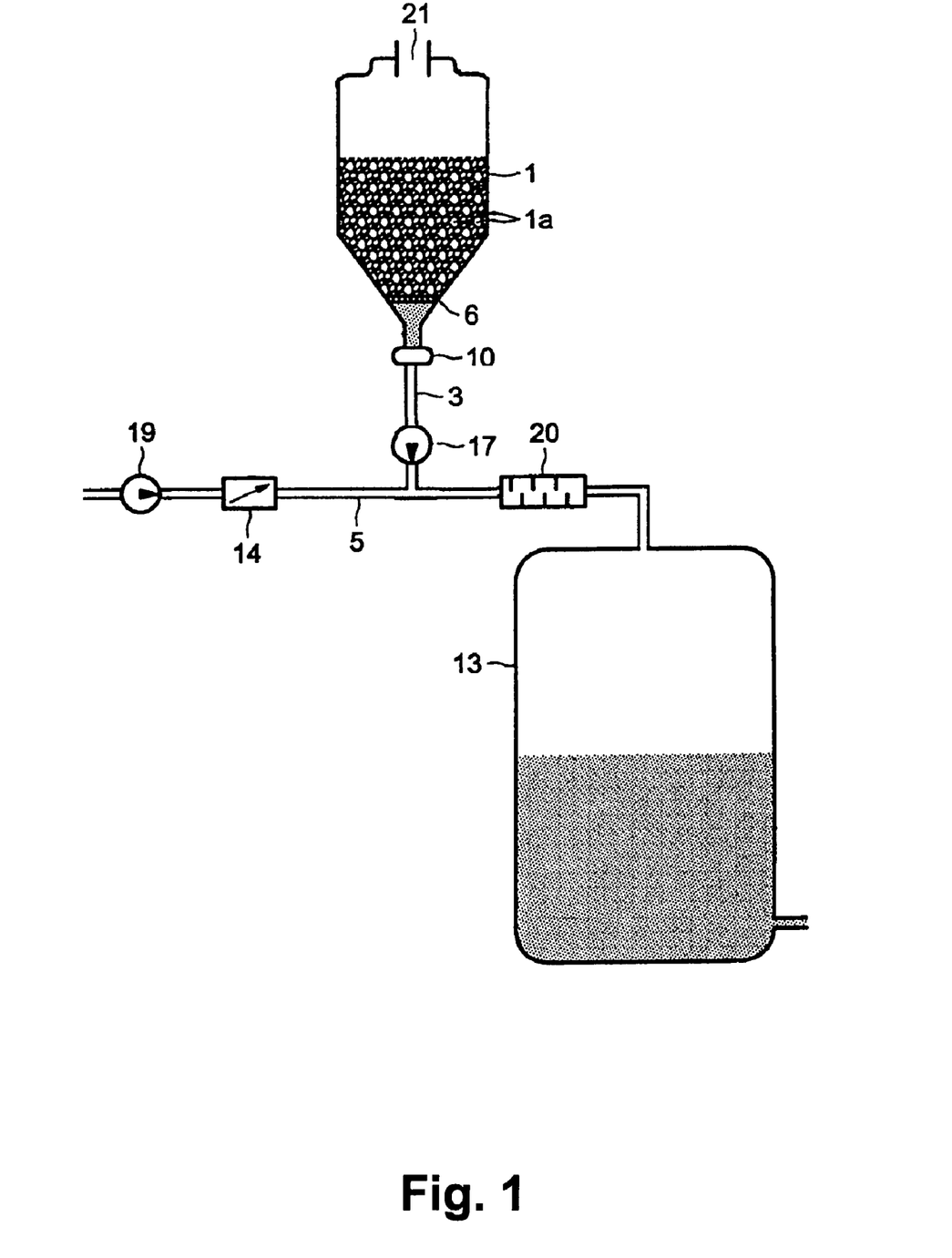
FIG. 1 is a schematic view of a device for inoculating the fermentation medium of a fermentation unit according to the first aspect of the invention.
Figure 2:
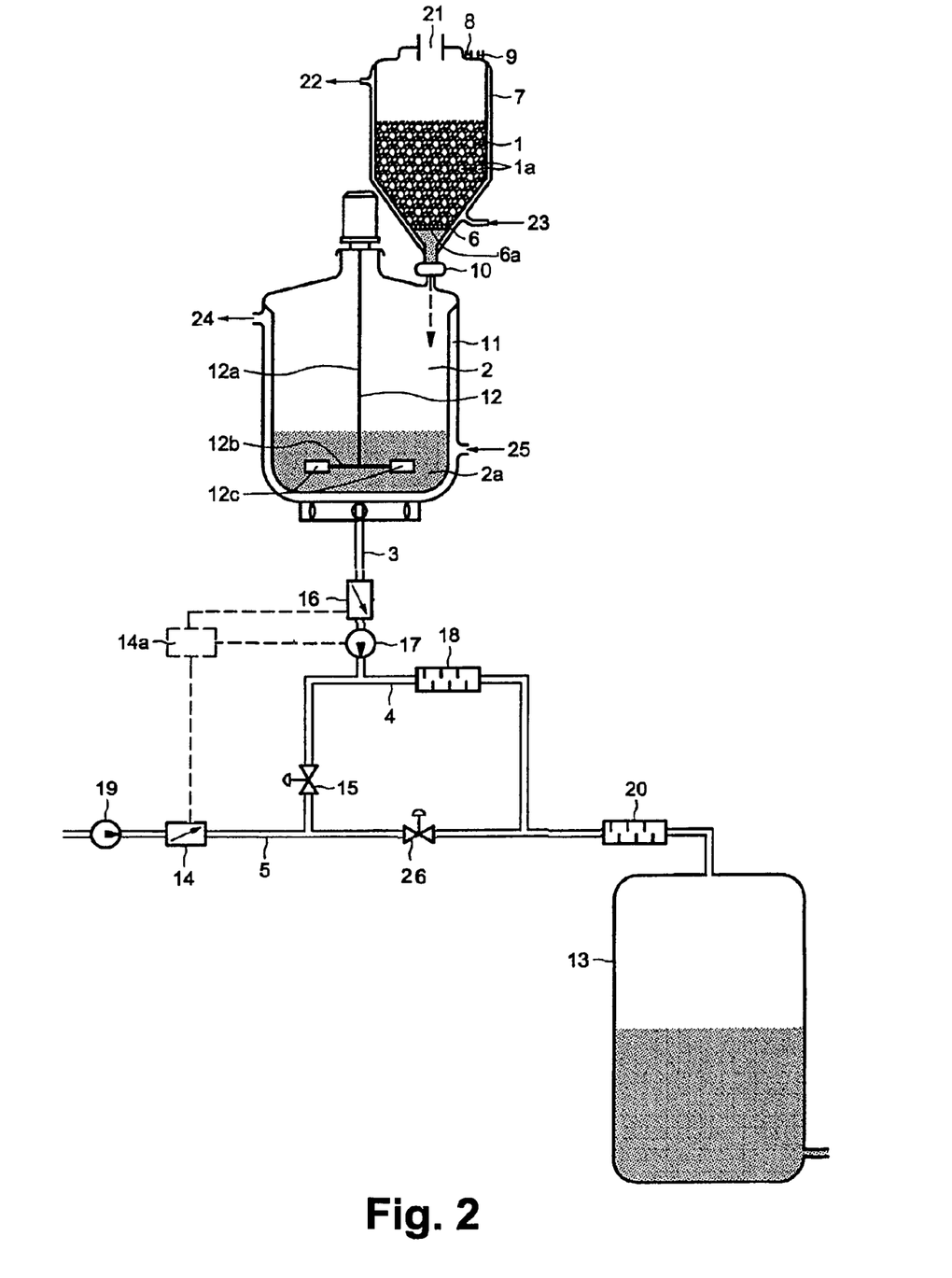
FIG. 2 is a schematic view in section of a preferred embodiment of the dosage device according to the invention.
Figure 3:
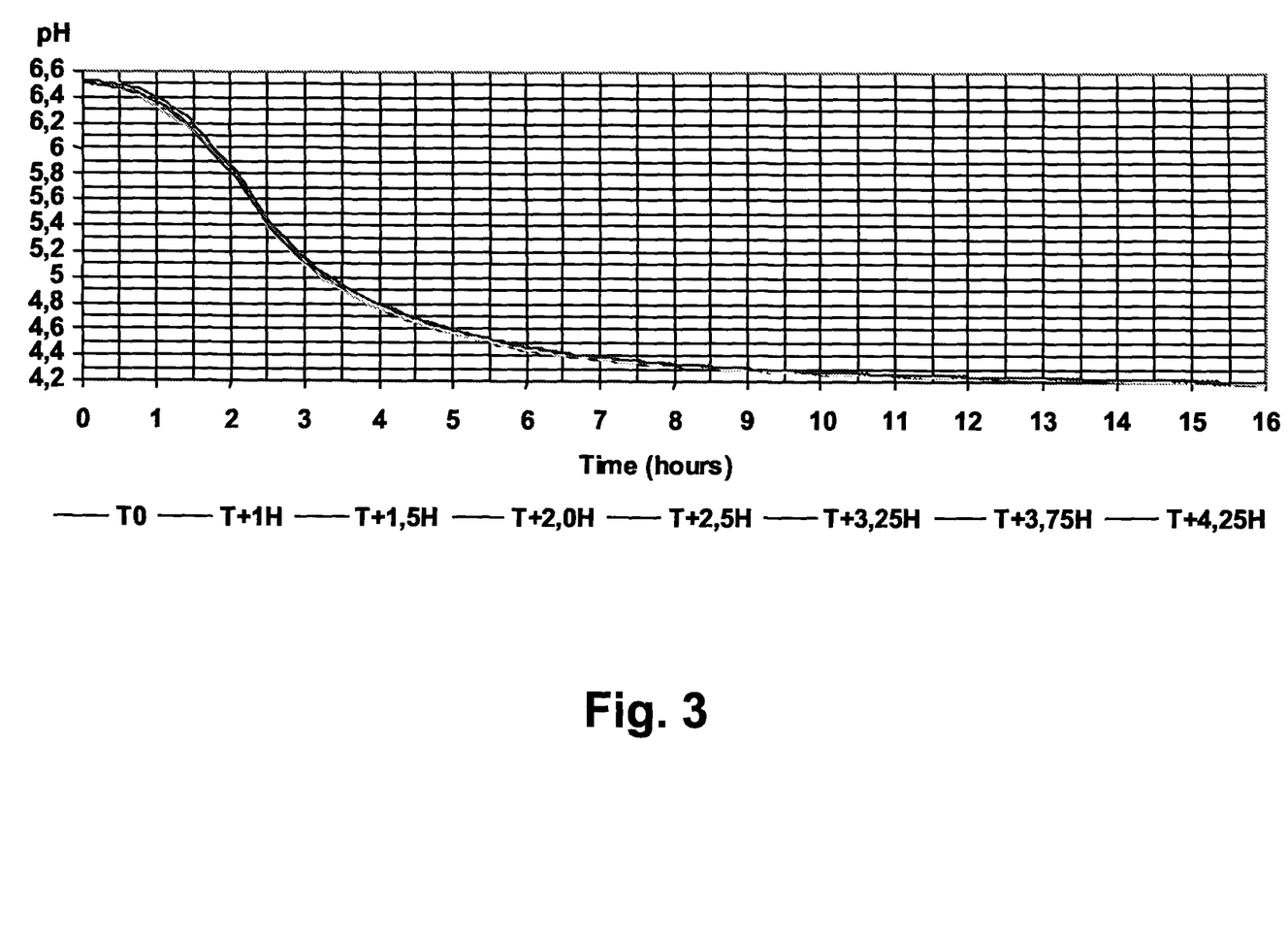
FIG. 3 is a curve monitoring the activity at 40° C. of the AP15 culture as a function of the storage time in thawed form. Storage times of 0, 1, 1.5, 2, 2.5, 3.25, 3.75 and 4.25 hours in the storage container (2) were evaluated. For each storage time, the acidification curve is shown. The acidification curve shows the change in pH in the fermentation media over a time period of 16 days.
Figure 4:
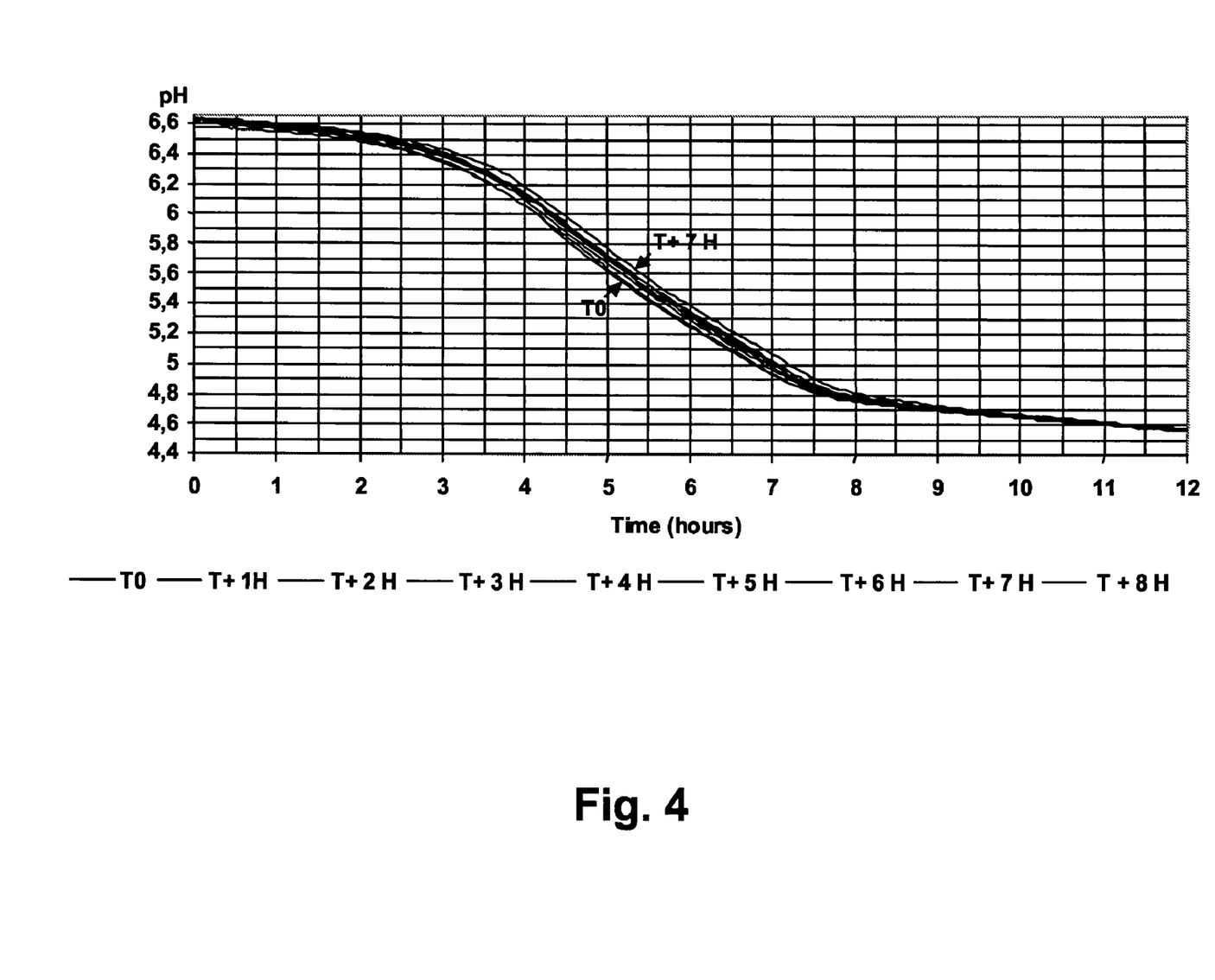
FIG. 4 is a curve monitoring the activity at 30° C. of the FMD-0046 culture as a function of the storage time in thawed form. Storage times of 0, 1, 2, 3, 4, 5, 6, 7 and 8 hours in the storage container (2) were evaluated, and the acidification curves are shown. The acidification curve shows the change in pH in the fermentation media over a time period of 12 days. The acidification curves for cultures stored at 0 and 7 hours are indicated by arrows.
Figure 5:
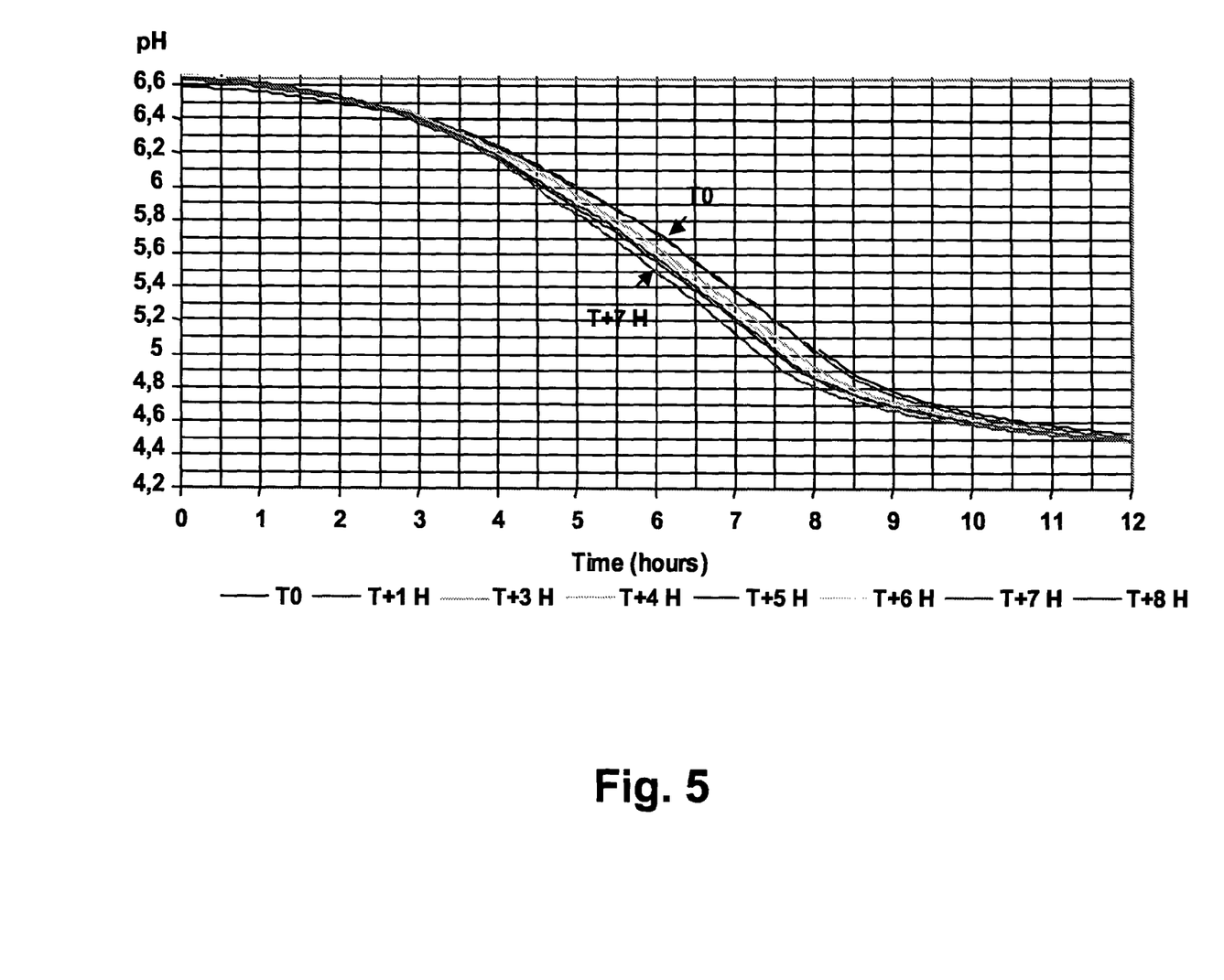
FIG. 5 is a curve monitoring the activity at 30° C. of the R604 culture as a function of the storage time in thawed form. Storage times of 0, 1, 2, 3, 4, 5, 6, 7 and 8 hours in the storage container (2) were evaluated, and the acidification curves are shown. The acidification curve shows the change in pH in the fermentation media over a time period of 12 days. The acidification curves for cultures stored at 0 and 7 hours are indicated by arrows.
Figure 6:
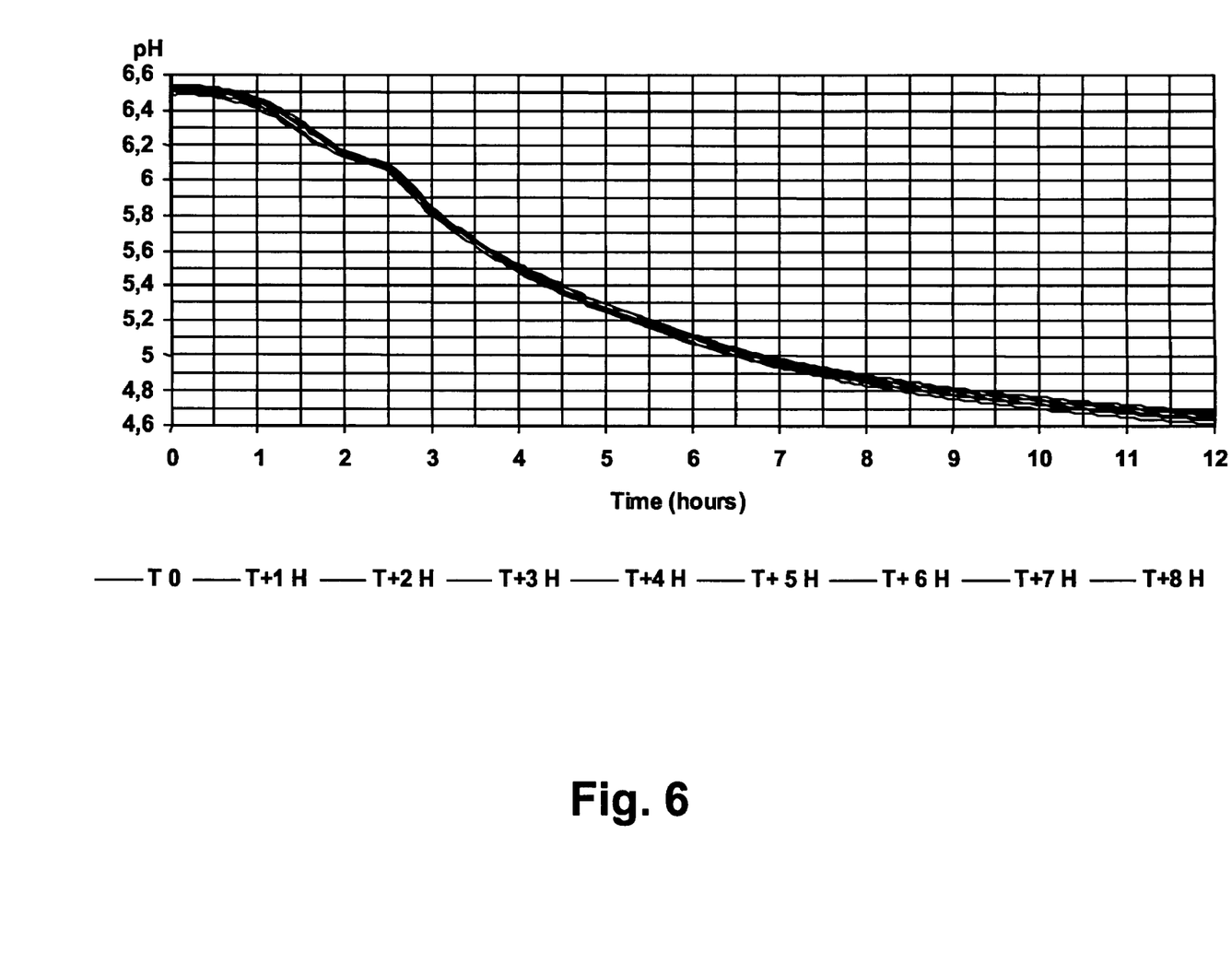
FIG. 6 is a curve monitoring the activity at 40° C. of the SSC1 culture as a function of the storage time in thawed form. Storage times of 0, 1, 2, 3, 4, 5, 6, 7 and 8 hours in the storage container (2) were evaluated, and the acidification curves are shown. The acidification curve shows the change in pH in the fermentation media over a time period of 12 days.
Figure 7:
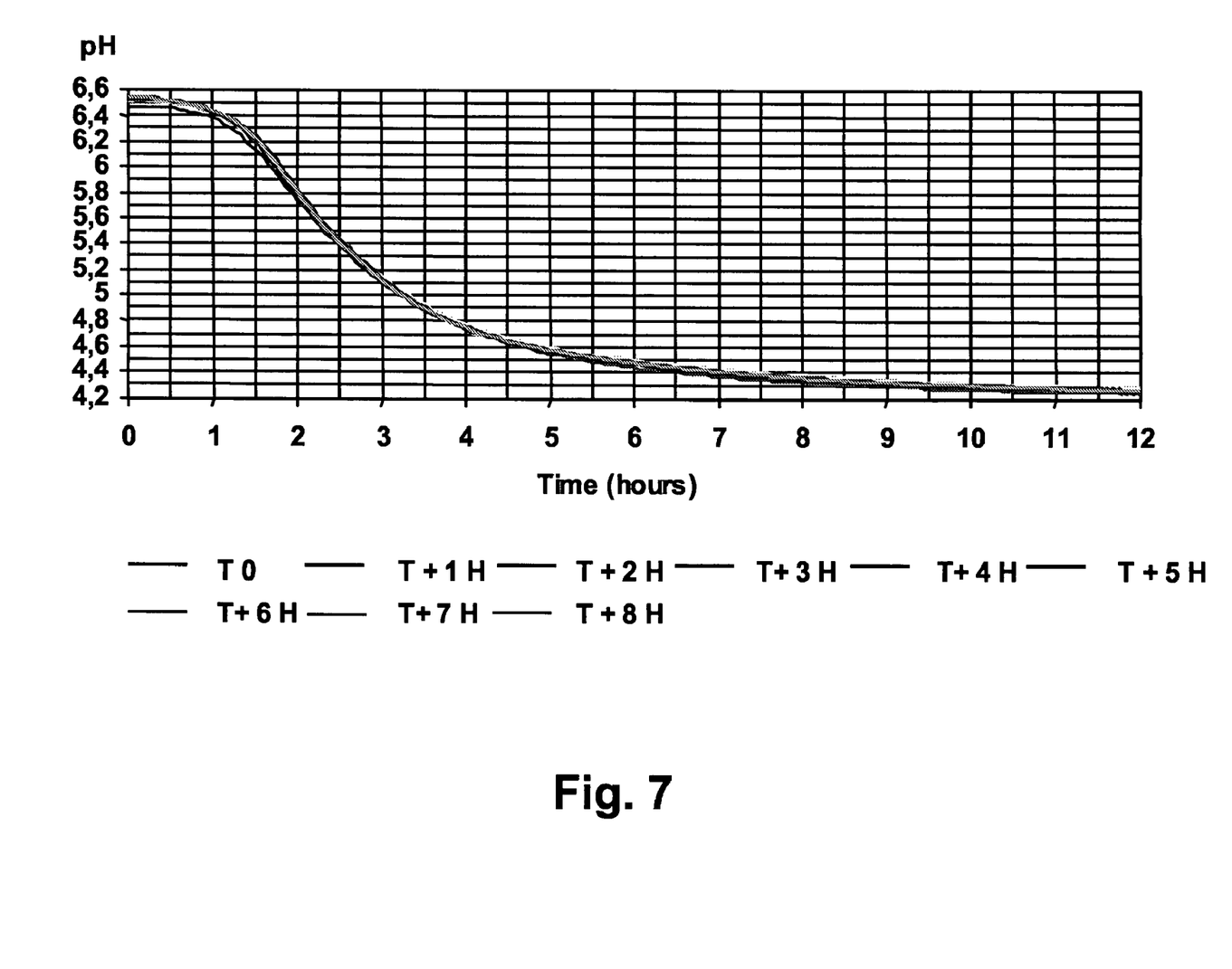
FIG. 7 is a curve monitoring the activity at 40° C. of the STM5 culture as a function of the storage time in thawed form. Storage times of 0, 1, 2, 3, 4, and 5 hours in the storage container (2) were evaluated, and the acidification curves are shown. The acidification curve shows the change in pH in the fermentation media over a time period of 12 days.
Figure 8:
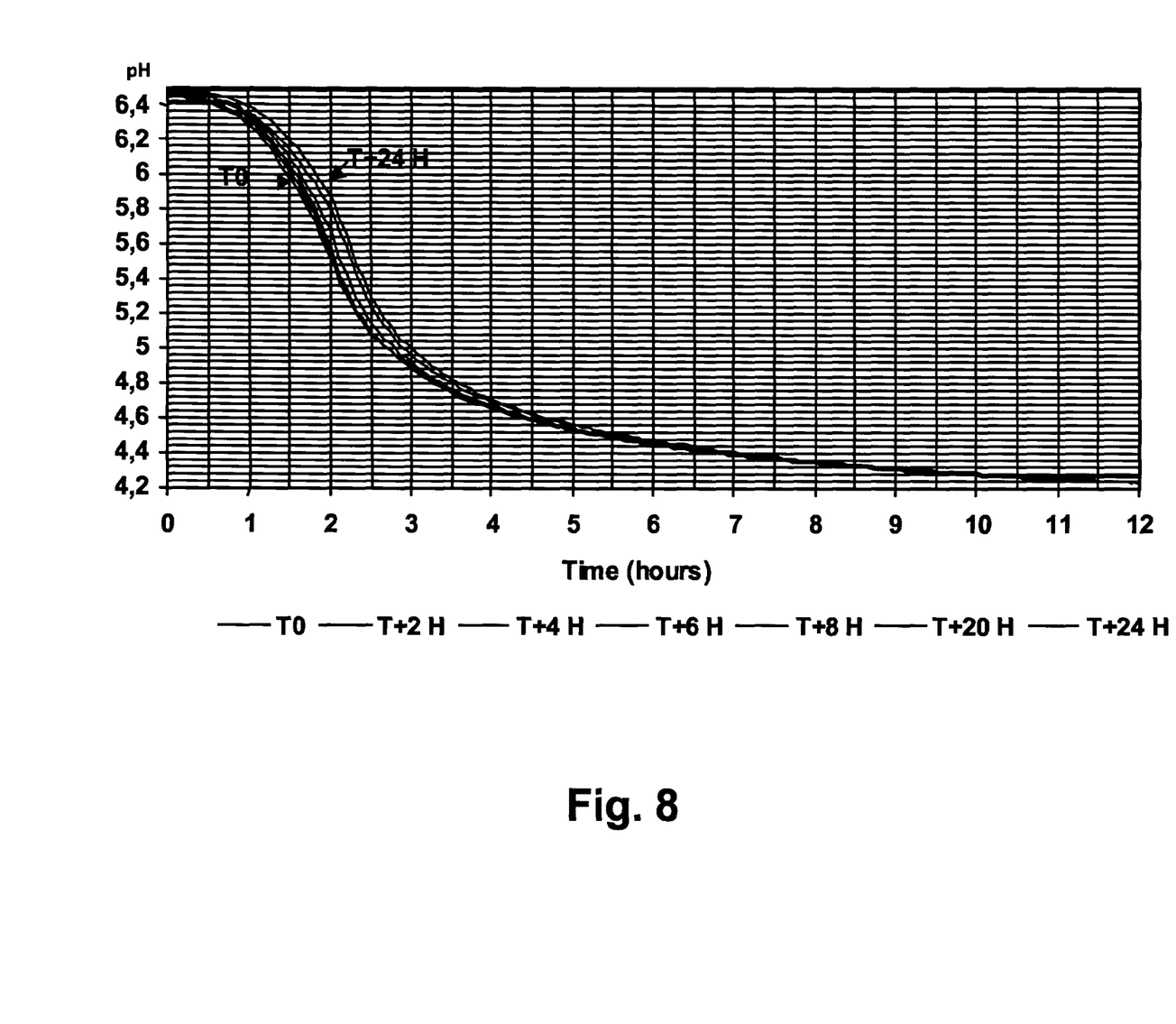
FIG. 8 is a curve monitoring the activity at 44° C. of the YF-L703 culture as a function of the storage time in thawed form. Storage times of 0, 2, 4, 6, 8, 20 and 24 hours in the storage container (2) were evaluated, and the acidification curves are shown. The acidification curve shows the change in pH in the fermentation media over a time period of 12 days. The acidification curves for cultures stored at 0 and 24 hours are indicated by arrows.

In FIG. 2, a device for inoculating the fermentation medium of a fermentation unit, which comprises a thawing container (1) containing frozen concentrated cultures in the form of frozen pellets (1a), and a storage container (2) containing the thawed concentrated cultures in liquid form (2a), the container (1) and the storage container (2) connected by a removable connection (10). The storage container (2) is connected by means of a conduit (or pipe) (3) to an inoculation conduit (4) branched from a main conduit (5) of the circuit feeding the liquid fermentation medium to be inoculated.

The thawing container (1) intended to melt the frozen concentrated cultures comprises at the bottom end a conical portion oriented downwards, said conical portion being provided with a rigid mesh or grille equipped with openings (6a). This mesh or grille (6) retains the frozen concentrated cultures (1a) inside the thawing container (1) while allowing the thawed culture to pass into the storage container (2). The thawing container (1) comprises a peripheral double wall (water jacket) (7) inside, where hot water can circulate in order to adjust the temperature of the thawing container (1) with the purpose of melting the frozen concentrated cultures (1a) in a controlled fashion. The hot water enters the water jacket through the inlet (23) at the bottom of the thawing container (1) and leaves again through the discharge (22) at the top of the thawing container (1). The thawing container (1) is also located at the top end with an inert sterile gas inlet (8) and a pressure safety valve (9) close to the inlet (8). The thawing container (1) is also equipped, at its top end, with an inlet (21) allowing the entry of concentrated cultures in frozen form.

The storage container (2) comprises a double wall (water jacket) (11) in which a cold liquid circulates. The cold water enters the water jacket through the inlet (25) at the bottom of the storage container (2) and leaves again through the opening discharge (24) at the top of the storage container (2).

The storage container (2) collects the liquid concentrated cultures, which flow through the openings in the grille or mesh (6) through the connection (10). The liquid concentrated cultures situated in the storage container (2) are stirred continuously by means of a stirrer (12) mounted for rotation inside the storage container (2). The stirrer (12) is composed of a vertical rod (12a) and a horizontal portion (12b) able to allow the stirring of the cultures (2a).

The stirrable lower part at the bottom of the storage container may for example be 5 liters of liquid concentrated cultures. The stirring can take place continuously or intermittently according to requirements. Other stirring modes are also possible, for example by means of a magnetic stirrer.

As demonstrated herein, it is possible to store several types of thawed concentrated starter cultures in the storage container (2) for several hours up to 24 hours without impeeding their activity, se example. However, preferably the cultures are stored between 4 and 8 hours in the storage container. From the example it will be appreciated that such storage can be performed without any particular damaging effect on the resumption of the bacterial metabolism and on the activity of the bacteria constituting the concentrated cultures.

The thawing container (1) and the storage container (2) can for example have a content of 30 to 50 liters.

The main conduit (5) used to fill a fermentation unit (13) comprises an optional pump (19) upstream of a flow meter (14) situated upstream of the bypass conduit (4) and an optional valve (26). In this embodiment, the fermentation unit is a fermentor. Naturally, in other embodiments, the fermentation unit may be a vessel for manufacturing fermented products or a device for fermentation directly in the container intended to be sold to the end-consumer, a dairy product cup, for example.

The bypass conduit (4) comprises a valve (15) upstream of the junction of the said bypass conduit (4) with the conduit (3) connected to the storage container (2). The conduit (3) mounted downstream of the storage container (2) comprises a flow meter (16) upstream of a pump (17) serving to regulate the flow rate of liquid concentrated cultures from the storage container (2). The conduit (4) also comprises, downstream of the conduit (3), a mixing chamber (18). Downstream of the junction with the conduit (5), the conduit (4) comprises a mixing chamber (20) mounted upstream of the fermentation unit (13).

The functioning of this starter culture dosage device is as follows: the frozen concentrated cultures are introduced in the form of pellets into an inlet (21) situated in the thawing container (1). These frozen concentrated cultures are thus poured thorough the inlet (21) into the thawing container (1).

The melting of these frozen concentrated cultures, which rest on the perforated rigid grille or mesh (6), takes place in the enclosure of this thawing container (1), whose walls are heated by means of hot water circulating in the enclosure (7). Thus, the frozen concentrated cultures resting on the bottom grille of the thawing container (1) flow into the storage container by means of the passage (10), the frozen concentrated cultures once melted are in liquid form in the storage container (2). The water jacket (11) allows the circulation of a cooling liquid.

The dosage of the melted product is an essential part of the fermentation unit inoculation method. This dosage is provided in two stages, first of all, from the main circuit (5), part of the medium that is to be inoculated is taken off continuously through the valve (15). This bypass circuit (4) containing the liquid to be inoculated is inoculated by the liquid concentrated cultures contained in the storage container (2) by means of a precise dosage pump (17) controlled by the flow meters (14) and (16) via the regulation device (14a).

The medium to be inoculated by the bypass feed circuit typically represents between 0.5 and 2% of the total medium to be inoculated of the main circuit.

The dosage pumps used such as the pump (17) can be sized according to the flow rate of the main circuit of the inoculated medium; typically, in the dairy industry, the flow rates of the dosage pumps vary from 0.1 l/hour to 4 l/hour for installations of 2 to 10,000 l/hour up to 0.75 l/hour to 12 l/hour for installations of 15,000 to 30,000 l/hour.

In this bypass conduit (4), the mixing of the melted concentrated starter culture with the medium to be inoculated takes place in the mixing chamber (18) in order to ensure perfect homogeneity of the inoculation. The first mixing takes place immediately after the dosage pump, the second mixing just after the injection from the bypass line into the main flow of the product.

In all the embodiments of the invention, the dosage device makes it possible to obtain precise on-line dosage of a small quantity of concentrated cultures from frozen concentrated cultures in order to inoculate the fermentation medium of a fermentation unit.

EXAMPLE 1

Stability of the Frozen Concentrated Cultures in Liquid Form

Various cultures in the form of frozen concentrated cultures are introduced successively into a melting vessel. The temperature of the water used for heating the enclosure is less than or equal to 40° C. and makes it possible to melt the mass of frozen concentrated lactic cultures in 30 minutes.

List of Cultures:

AP15 consisting of *Streptococcus thermophilus* used in hard cheeses of the Emmental type.

FMD-0046 consisting of a mixture of *Lactococcus lactis* subsp. *lactis*, *Lactococcus lactis* subsp. *cremoris*, *Lactococcus lactis* subsp. *lactis* biovar. *diacetylactis* and *leuconostoc cremoris* used in soft cheeses or cultured milks.

R604 consisting of *Lactococcus lactis* subsp. *lactis*, and *Lactococcus lactis* subsp. *cremoris* used in stabilized soft cheeses.

SSC1 consisting of a *Streptococcus thermophilus* mixture used in stretched-curd cheeses of the mozzarella type.

STM5 consisting of a *Streptococcus thermophilus* mixture.

YF-L703 consisting of a mixture of *Streptococcus thermophilus* and *Lactobacillus delbruckei* subsp. *bulgaricus* used in fermented milks of the set yoghurt type.

These cultures are distributed by the company Chr. Hansen A/S, Horsholm, Denmark.

The measurement of the acidifying activity was made according to the following protocol:

|  | Cultures | | | | | |
| --- | --- | --- | --- | --- | --- | --- |
|  | AP15 | FMD-0046 | R604 | SSC1 | STM5 | YF-L703 |
| Substrates | Skimmed milk reconstituted from skimmed milk powder with 10% dry matter | | | | | Skimmed milk reconstituted from skimmed milk powder with 12% dry matter |
| Incubation temperature in the enclosure (° C.) | 40° C. | 30° C. | 30° C. | 40° C. | 40° C. | 44° C. |
| Starter culture dose (g/100 L) | 10 | 10 | 10 | 10 | 10 | 20 |

The final dosage used is 0.01% or 0.02% and thus 10 or 20 grams of starter culture were weighed in order then to inoculate 100 liters of milk.

Sampling points for measuring the acidifying activity:

AP15:

| T0 | T + 1 H | T + 1 H 30 | T + 2 H | T + 2 H 30 | T + 3 H 15 | T + 3 H 45 | T + 4 H 25 |
| --- | --- | --- | --- | --- | --- | --- | --- |

I.e. sampling occurred after 0, 1, 1:30 (90 minutes), 2, 2:30, 3:15, 3:45 and 4:25 hours of storage in the storage container.

FMD0046-R604-SSC1-STM5:

| T0 | T + 1 H | T + 2 H | T + 3 H | T + 4 H | T + 5 H | T + 6 H | T + 7 H | T + 8 H |
| --- | --- | --- | --- | --- | --- | --- | --- | --- |

I.e. sampling occurred after 0, 1, 2, 3, 4, 5, 6, 7 and 8 hours of storage in the storage container.

YF-L703:

| T0 | T + 2 H | T + 4 H | T + 6 H | T + 8 H | T + 20 H | T + 24 H |
| --- | --- | --- | --- | --- | --- | --- |

I.e. sampling occurred after 0, 2, 4, 6, 8, 20 and 24 hours of storage in the storage container.

The results of the acidifying activity of each of the strains tested are presented in the figures in the form of curves showing the variation of the pH of the inoculated medium as a function of time.

As can be seen from the data presented in FIG. 3 to 8 the stability of the various strains tested is excellent. Thus, it is possible to conclude that there is only a minute effect of the storage time in the storage device on the acidifying activity performance of the cultures. Only in the experiment with the R604 (FIG. 5) and the YF-L703 (FIG. 7) a storage time dependant effect was evident.

We conclude that it hereby has been demonstrated that by using the present invention, it is possible to store various types of frozen starter cultures after they have been thawed for several hours up to 24 hours without any particular damaging effect on the resumption of the acidifying activity of the cultures.

The invention claimed is:

1. A device for the continuous dosage of a frozen starter culture into a liquid fermentation medium to be inoculated, wherein said device comprises (A) a fermentation unit and (B) a container for thawing of the starter culture, which container comprises means of retaining the frozen culture inside the thawing container while allowing the thawed liquid starter culture to pass into a circuit for the continuous feeding of the fermentation medium into the fermentation unit, wherein said circuit is provided with means of regulating a flow-rate of the culture in liquid form and a flow-rate of the fermentation medium.

2. The device according to claim 1, wherein the thawing container (1) comprises the means (6) of retaining the frozen culture and outlet openings (6a) for the culture in the liquid form and means (3) of connection to the circuit (4), for continuously feeding the liquid fermentation medium to be inoculated, the connection being provided by the means (17) of regulating the flow rate of the culture in liquid form.

3. The device according to claim 1, wherein said frozen culture is a concentrated frozen culture (1a) in the form of pellets or granules.

4. The device according to claim 1, wherein it comprises an intermediate storage container (2) for the culture inserted between the thawing container (1) and the means (17) of regulating the flow rate of the culture in liquid form.

5. The device according to claim 1, wherein said frozen culture is a concentrated frozen culture (1a) contained in a flexible enclosure placed inside the thawing container (1).

6. The device according to claim 1, wherein thawing container is connected to the storage container by a connection (10), such that the thawing container is removable.

7. The device according to claim 1, wherein the device comprises means (18) of mixing a predefined part of the culture with a predefined part of the liquid to be inoculated, mounted in the circuit (4) downstream of the flow rate regulation means (17) for the culture in liquid form.

8. The device according to claim 1, wherein the thawing container (1) comprises heating means (7).

9. The device according to claim 4, wherein the intermediate storage container (2) comprises cooling means (11).

10. The device according to claim 1, wherein the circuit (4) for feeding the liquid fermentation medium to be inoculated is connected as a bypass to a main circuit (5) for supplying the fermentation unit (13).

11. The device according to claim 4, wherein the intermediate storage container (2) for the thawed culture is provided with a stirrer (12).

12. The device according to claim 7, further comprising a mixing chamber (20) located between the means (18) of mixing and the fermentation unit, wherein an extra storage container is inserted between the mixing chamber (20) and the fermentation unit (13).

13. A method of dosing a frozen inoculant, wherein 1) frozen concentrated culture is thawed in a thawing container that comprises means of retaining the frozen culture inside the thawing container while allowing thawed liquid starter culture to pass, 2) the thawed culture is kept temporarily at low temperature and 3) a well-defined quantity of said thawed culture is introduced continuously into a flow of a liquid fermentation medium to be inoculated.

14. The method according to claim 13, wherein the thawing of the frozen concentrated culture occurs in a time between 10 and 60 minutes.

15. The method according to claim 13, wherein the thawed liquid culture is kept at a temperature of between 2 and 12° C.

16. The method according to claim 13, further comprising a storage container for the liquid starter culture, wherein the starter culture in the thawing container is subjected to a positive pressure inert gas atmosphere obtained by injection of an inert sterile gas into said thawing container.

17. The method according to claim 13, wherein said liquid fermentation medium is selected from the group consisting of milk, milk derived products, wine, juice and silage.

18. The method according to claim 13, wherein said frozen concentrated culture is a culture of Lactic Acid Bacteria.

19. The method according to claim 13, wherein the inoculated liquid fermentation medium is kept under starter culture fermenting conditions to obtain a fermented beverage, food or feed product.

20. The method according to claim 13, wherein the inoculated liquid fermentation medium is inoculated milk or milk-derived product and is kept under starter culture fermenting conditions to obtain a fermented dairy product.

* * * * *